(12) United States Patent
Nauert

(10) Patent No.: US 6,402,711 B1
(45) Date of Patent: Jun. 11, 2002

(54) KNEE BRACE OPERATING HINGE

(76) Inventor: Richard S. Nauert, 351 N. Newport Blvd., No. 120, Newport Beach, CA (US) 92663

( * ) Notice: Subject to any disclaimer, the term of this patent is extended or adjusted under 35 U.S.C. 154(b) by 0 days.

(21) Appl. No.: 09/371,157

(22) Filed: Aug. 10, 1999

(51) Int. Cl.$^7$ .................................................. A61F 5/00
(52) U.S. Cl. .......................................... 602/16; 602/26
(58) Field of Search .............................. 602/5, 16, 20, 602/23, 26; 16/354; 403/52, 57, 62, 81; 623/39; 446/378

(56) References Cited

U.S. PATENT DOCUMENTS

| | | | |
|---|---|---|---|
| 4,506,661 A | * 3/1985 | Foster | 602/26 |
| 4,628,916 A | * 12/1986 | Lerman | 602/26 |
| 4,732,143 A | * 3/1988 | Kausek et al. | 602/16 |
| 4,791,916 A | * 12/1988 | Paez | 602/26 |
| 4,986,264 A | 1/1991 | Mason et al. | |
| 5,038,763 A | * 8/1991 | Wiggins | 602/16 |
| 5,213,094 A | * 5/1993 | Bonutti | 602/16 |
| 5,230,696 A | 7/1993 | Silver et al. | |
| 5,288,287 A | 2/1994 | Castillo et al. | |
| 5,443,444 A | * 8/1995 | Pruyssers | 602/26 |
| 5,693,007 A | 12/1997 | Townsend | |
| 5,743,865 A | 4/1998 | Townsend | |
| 5,782,780 A | 7/1998 | Mason et al. | |
| 6,001,075 A | * 12/1999 | Clemens et al. | 602/16 |
| 6,066,110 A | 5/2000 | Nauert | |

FOREIGN PATENT DOCUMENTS

JP             025478 A * 2/1990 ................. 16/354

* cited by examiner

Primary Examiner—Denise Pothier
(74) Attorney, Agent, or Firm—Curtis L. Harrington

(57) ABSTRACT

A brace hinge includes an upper and lower intermeshing gear members each having an elliptical gear intermeshed with the other and sandwiched by two very thin profile cover and support plates. The elliptical gears produce an eccentric motion which lends it self to following the natural motion of the human knee or other joints such as the elbow. The elliptical gear of one member has its radius extend toward the pivot axis of the other gear as the radius of the other elliptical gear retreats from the pivot axis of the one member. The magnitude and radial extent over which the ellipse extends can be varied. The combination of advancing and retreating radius gear members, relatively few gear teeth and sandwiched support plates eliminate any interruption to a smooth transition, provide superior load bearing ability and provide for extremely low friction.

14 Claims, 2 Drawing Sheets

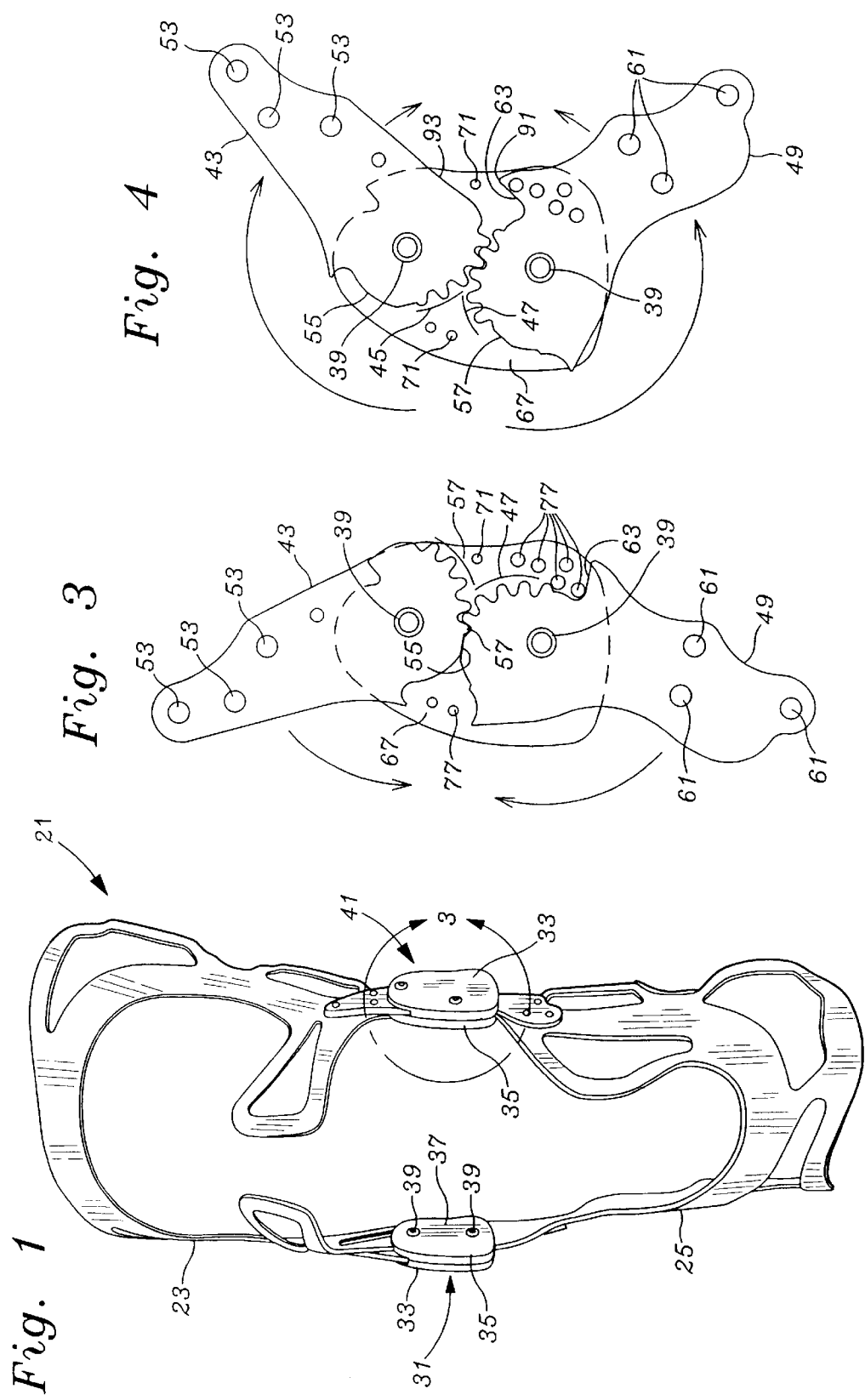

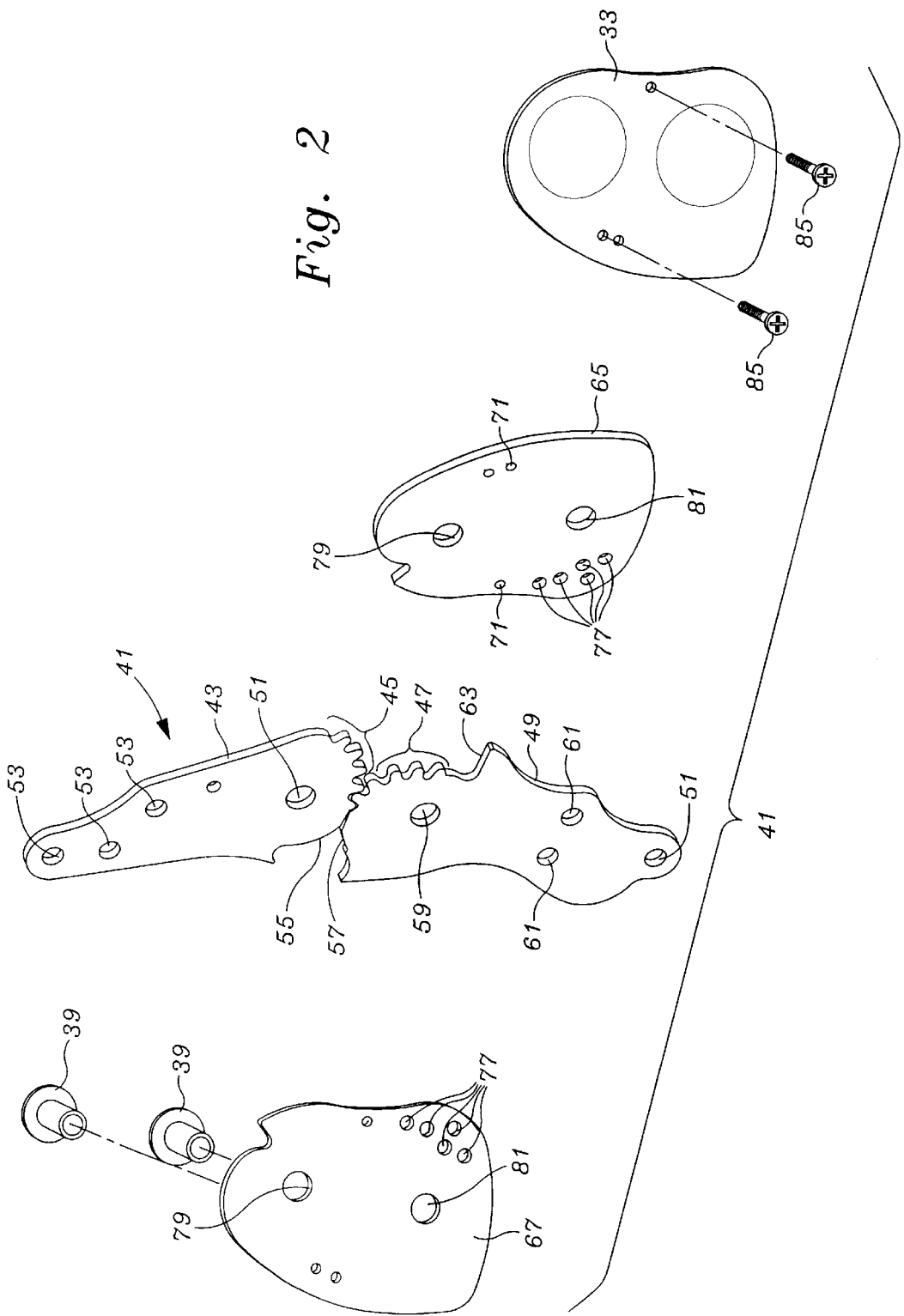

KNEE BRACE OPERATING HINGE

FIELD OF THE INVENTION

The present invention relates to an improved, gear mechanism for controlling the motion and angular displacement of upper and lower members of a leg brace for the stabilization and control of a human knee joint of the left and or the right leg, and more particularly to a pair of intermeshing perpendicular elliptical gears, one invading and the other retreating, and including structure for limiting the angular displacement of the gear.

BACKGROUND OF THE INVENTION

The prior art describes many orthopedic devices which attempt to support and stabilize the human knee over a wide range of angular, lateral and rotational displacement of the human leg. However, in most cases high integration of a motion controlling structure produces a non-smooth operation. In U.S. Pat. No. 4,773,404 to Jeffrey H. Townsend one of the hinge members is required to snap sharply in one direction before pivoting can take place. This is also described in U.S. Pat. No. 5,330,418 to Jeffrey H. Townsend. In U.S. Pat. No. 4,940,044 to Castillo, the hinge is placed so far forward of the axis of pivot of the leg that the device does little more than tenuously accommodate a pivot connection between the upper and lower cuff members.

In all of these cases, a smooth control between the upper and lower cuffs of a leg brace is simply not obtainable. The use of two circular gears alone would not provide a movement which is more supportive to the leg joint throughout its angular displacement. A simple single or double circular gear cannot produce a motion which closely follows the arc of rotation of the human knee which is based upon the cam shaped condyles of the human femur. This cam shape is commonly referred to as the sagittal plane in the orthopedic profession and commonly varies only slightly from person to person. This movement path is generally described as being of a lesser radius or flatter curve at the initiation of movement and thence transitioning into an increasingly tighter, yet relatively constant radius motion. The above described hinges are clumsy attempts to provide a hinge which provides a shifting radius throughout the angular displacement of the hinge to truly track the motion of the human knee.

Another drawback of the hinges, such as those referred to above is the use of pins traveling in slots. These devices create additional friction through extended friction surfaces and concentrate the force in the pins sliding in the slots.

Another problem with currently available hinges is their width profile. Most two component hinges have overlapping members supported from one side, or have mutual support between the overlapping members. The width is bulky and the extension, even when not in flexion, is such that it must be worn with looser clothing. In flexion, the protrusion in the direction toward the front of the knee is severe and even more space and looser clothing is required. In addition, forward extension during flexion increases the probability that the brace will be caught or snagged on other objects, or as clothing is damaged from being stretched across the protruding hinge.

What is therefore needed is a hinge which enables guided controlled movement support of the knee, which is as friction free as possible. The needed hinge should be able to bear significant weight without binding and should produce a motion which is as close as possible to the movement of the human leg and which eliminates pin in slot structures.

SUMMARY OF THE INVENTION

The brace hinge of the present invention includes an upper and lower intermeshing gear members each having an elliptical gear intermeshed with the other and sandwiched by two very thin profile cover and support plates. The elliptical gears produce an eccentric motion which lends it self to following the natural motion of the human knee or other joints such as the elbow other motion of other joints can be mimicked as needed by varying the shape of the ellipses of the gears used in the hinges and further utilizing an ellipse which actually increases desirable forces during the motion of the hinge to increase the performance of the brace. The user's knee, or other joint, will track in a correct natural arc and will be controlled by the brace having the hinges of the invention applying controlling forces to the knee or other joint to prevent its deviation from its correct and natural path.

The elliptical gear of one member has its radius extend toward the pivot axis of the other gear as the radius of the other elliptical gear retreats from the pivot axis of the one member. The magnitude and radial extent over which the ellipse extends can be varied. The combination of advancing and retreating radius gear members, relatively few gear teeth and sandwiched support plates eliminate any interruption to a smooth transition, provide superior load bearing ability and provide for extremely low friction. Because of the planar and close fitting of the surfaces between the cover and support plates and the upper and lower gear supports the hinge can hold lubrication for an extended period. The hinge members can be constructed of plastic, ceramic, metal, metal matrix composite or any combination thereof. The mesh points of the gear teeth provide a constant force there between along a line drawn from one rotational or pivot center to the other. The ellipses reciprocally compensate and they gain and withdraw the mesh interface moves from one gear support pivot point to the other.

The elliptical advancing and retreating interface is protected and stabilized by support and stabilization plates. The specific characteristics of the elliptical gears can be custom formed by the user or technician to even more closely follow the leg angular displacement motion and knee characteristics of a given user. Although the embodiment herein illustrates a 0° to 180° angular displacement of the hinge, other displacement ranges can be provided.

The cover and support plates form a seemingly center link and retract through flexion relative to the farthest forward point of the knee when viewed from the side. This creates a slimmer profile for the brace at the hinge level when viewed in the horizontal plane.

BRIEF DESCRIPTION OF THE DRAWINGS

The invention, its configuration, construction, and operation will be best further described in the following detailed description, taken in conjunction with the accompanying drawings in which:

FIG. 1 is a perspective view of a left leg brace including the hinges of the invention;

FIG. 2 is an exploded view of the outside hinge of the left leg brace seen in FIG. 1 and illustrating upper and lower gear supports having elliptical gears with an elliptical and limited progression of gear teeth;

FIG. 3 is a partially assembled view of the hinge of FIG. 2 in an un-flexed position; and FIG. 4 is the left hinge of FIG. 3 shown in a flexed position.

DETAILED DESCRIPTION OF THE PREFERRED EMBODIMENT

A description of the improved brace of the present invention will be best initiated with reference to FIG. 1. A brace 21 has an upper main support 23 and a lower main support 25. This type of brace 21 upper and lower main support 23 and 25 is formable to more closely fit the leg of the user. Close interfitting enables the brace 21 to provide a more exacting degree of support and thus the operation of the hinged movement is important to maintaining control.

A right hinge 31 includes an outer cover 33 having a forward surface 35. An inside plate 37 is seen supporting the heads of two rivets 39. A left hinge 41 is also seen having similar structure.

Referring to FIG. 2, an exploded view of the left hinge is shown and further details of the structure is seen. An upper gear support 43 has a set of gears 45 which intermesh with a set of gears 47 of a lower gear support 49. Note that the upper gear support 43 attaches to the inside of upper main support 23 while the lower gear support 49 attaches to the inside of the lower main support 25.

Upper gear support 43 includes an upper pivot aperture 51, and a series of upper rivet apertures 53. The upper gear support 41 has a smooth section 55 at the end of the gears teeth 45 in order to limit the movement of the upper gear support 43 with respect to the lower gear support 49. Similarly, the lower gear support 49 contains a smooth section 57 opposing the smooth section 55 of the upper gear support 43. Lower gear support 49 includes a lower pivot aperture 59. Lower gear support 49 also contains a series of lower rivet apertures 61.

The lower gear support 49 contains a stop structure 63 which will be used to limit the motion of the hinge 33 if so desired, as will be shown. To the right of the upper and lower gear supports 43 & 49 is a first cover and support plate 65, and to the left of the upper and lower gear supports 49 is a second cover and support plate 67. The hinge 31, especially since it is riveted, could operate with only one of the first and second cover and support plates 67 and 67, but the use of two gives greater stability. First and second gear cover and support plates 65 and 67 are preferably identical. To the left of second cover and support plate 67, a pair of rivets 39 are seen in an orientation before bending the ends thereof. The structures on the first and second cover and support plates 65 & 67 are identical. First and second cover and support plates 65 & 67 include apertures 71 for securing the cover 33 onto the outermost one of the first and second cover and support plates 65 & 67, which in this case is second cover and support plate 65. Aperture 71 can accept a screw 85 for assisting the first and second cover and support plates 65 & 67 together.

First and second cover and support plates 65 & 67 include a correspondingly opposing set of limit stop apertures 77 which act in concert with stop structure 63 to limit the extent to which the hinges 31 will angularly displace. A screw is placed in one of the apertures 77 corresponding to the extent to which angular displacement is limited. First and second cover and support plates 65 & 67 & each have an upper pivot rivet aperture 79 and a lower pivot rivet aperture 81. Once the upper and lower gear supports 43 and 49 and their upper and lower pivot rivet apertures 81 are joined on the two rivets 39 extending through one of the first and second cover and support plates 65 & 67, the relative rotational position of each are locked.

Note that the use of apertures 79 and 81 combined with joinder by rivets 39 could be replaced by a system in which the first and second cover and support plates 65 & 67 included interlocking structure, such as an annular projection or even a projection integrally formed with one of the plates 65 and 67 in order to engage upper and lower pivot apertures 51 and 59. Alternatively, the upper and lower gear supports 43 and 49 could be fitted with a projection to engaged the apertures 79 and 81 of the first and second cover and support plates 65 & 67. All of these structures, as well as other structures, could be employed to provide a stable pivoting support of the upper and lower gear supports 43 and 49.

Since each of the upper and lower gear teeth sections 45 and 47 contain a limited number of teeth, and since the gear sections are elliptical, the rotational lock is positive. It is impossible to fit the gear teeth sections 45 and 47 together in a mis-aligned fashion. Because the gear teeth section 45 of the upper gear support 43 increases it radial distance to the lower pivot aperture 59 while the gear teeth section 47 of the lower gear support 49 reduces its radial distance to the upper pivot aperture 51, the relative position of the supports 43 and 49 is exactly fixed. The position and depth of each gear tooth and each valley is known and is an exact fit. The teeth sections 45 and 47 can never fall out of alignment.

It is understood that the radial elliptical starting and finishing points of the gear sections 45 and 47 can extend over a radially increased or radially decreased range to provide for greater or lesser angular displacement over the full range of the hinge 31. For a given severity of elliptical radius change over any radial range, the complex motion of the hinge 31 can be varied. Because the upper and lower gear supports 43 and 49 are so simple in their structure as flat plates, a custom brace motion can be computed based upon individual leg size and characteristics and custom made upper and lower gear supports 43 and 49, with individually specifiable teeth 45 and 47 elliptical characteristics can be machine formed inexpensively and in a short time.

To the right of FIG. 2 the cover 33 is seen in relationship with two screws 85 for securing it to the cover and support plate 65.

Referring to FIG. 3, a view of upper gear support 43 and lower gear support 49 intermeshed together and shown with respect to second cover and support plate 67. The upper gear support 43 and lower gear support 49 are in a position where they are most linear, in the un-flexed position. The structural portion extending away from the rivets 67 are not particularly straight, but the shape of such structure will be dependent upon the matching shape of an upper and lower main support 23 and 25 to which it is to be attached. The smooth sections 55 and 57 are seen in an interfering relationship preventing the upper gear support 43 and lower gear support 49 from pivoting further in the direction of the smooth sections 55 and 57. The limit stop apertures 77 are seen in position just in front of the stop structure 63. As can be seen, the radial extent of the gear set 47 on a line between the rivets 39, is closer to the rivet 39 of the upper gear support 43.

Referring to FIG. 4, a view taken with respect to the viewing perspective of FIG. 3 illustrates the upper gear support 43 and lower gear support 49 intermeshed together and shown in flexion. A tip end 91 of the stop structure 63 of upper gear support 43 is about to make contact with a side surface 93 of the lower gear support 49 to limit the flexion of the hinge 41. As can be seen, the stop structure 63 is shown as having swept past all of the limit stop apertures 77, any one of which could have contained a screw, or pin or other blocking object to engage the stop structure 63 to limit flexion.

Note in FIG. 4 that the radial extent of the gear set 47 on a line between the rivets 39, is closer to the rivet 39 of the lower gear support 49. FIGS. 4 and 5 taken together illustrate the action of the elliptical gear sets 45 and 47. By shifting the rotation interface from a position closer to one pivot axis that the other before flexion, and in a continuous path toward the other pivot axis at the termination of flexion, a motion which is more natural to the knee or other joint is obtained. The rapidity of the transition will depend upon the severity of the ellipse upon which the gear sets 45 and 47 are based, as well as the shape of the gears and their contact during the pivot action.

While the present invention has been described in terms of an opposing elliptical gear set for use with leg brace, one skilled in the art will realize that the structure and techniques of the present invention can be applied to many similar structures. The present invention may be applied in any situation where the axis of movement is to be changed throughout the movement range in manner which is as smooth and frictionless as possible while deriving significant control forces from the hinge.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. A knee brace hinge comprising:

a first gear support having a first end, and a second end and a first pivot aperture near said second end and having a first set of gear teeth arranged to at least one of increase and decrease about a radial distance in a first direction, at said second end and radiused with respect to said first pivot aperture;

a second gear support having a first end and a second end and a second pivot aperture near said second end and having a second set of gear teeth arranged to at least the other of increase and decrease about a radial distance in a second direction, and such that said first set of gear teeth are complementary to said second set of gear teeth to permit flexure of said first gear support with respect to said second gear support, at said second end and radiused with respect to said second pivot aperture, said first pivot aperture having a fixed distance from said second pivot aperture;

a cover and support plate for providing adjacent support to said first and said second gear supports and having a first support aperture in alignment with said first pivot aperture of said first gear support and a second support aperture in alignment with said second pivot aperture of said second gear support; and pivot support structures extending through said first and second support apertures and said first and second pivot apertures for pivotably supporting said first and second gear supports in a pivoting relationship with said cover and support plate, said pivot support structures, cover and support plate and said first and second gear supports forming a first hinge; and wherein said first and said second set of gear teeth have an elliptical arrangement, and wherein said first end of said first gear support and said first end of said second gear support includes attachment structure for attaching said hinge to an upper and a lower brace support, said first set of gear teeth radially increasing with respect to said first pivot aperture and said second set of gear teeth radially decreasing with respect to said second pivot aperture such that said first set of gear teeth radially increase while said second set of gear teeth radially decrease upon flexing of said first and second gear supports relative to each other.

2. The hinge for a knee brace as recited in claim 1 wherein said pivot support structures are rivets.

3. The hinge for a knee brace as recited in claim 2 and further comprising:

a second hinge having first and second gear supports;

an upper brace support having a first side connected to said first gear support of said first hinge and a second side connected to said first gear support of said second hinge; and an lower brace support having a first side connected to said second gear support of said first hinge and a second side connected to said second gear support of said second hinge, said upper and lower braces with said first and second hinges forming a leg brace.

4. The hinge for a knee brace as recited in claim 1 wherein said first and said second set of gear teeth have an elliptical progression arrangement.

5. The hinge for a knee brace as recited in claim 1 wherein, as said first gear support is angularly displaced with respect to said first gear supports, a gear engagement radial distance of one of said first and said second set of gear teeth are arranged to increase as a gear engagement radial distance of the other of said first and second set of gear teeth are arranged to decrease.

6. The hinge for a knee brace as recited in claim 5 wherein said one of said first and said second set of gear teeth is said first set of gear teeth and wherein the other of said first and said second set of gear teeth is said second set of gear teeth.

7. The hinge for a knee brace as recited in claim 1 wherein said first set of gear teeth lie adjacent a first smooth section of said first gear support and where said second set of gear teeth lie adjacent a second smooth section of said second gear support which interfere with said first smooth section to limit pivoting of said first gear support with respect to said second gear support.

8. The hinge for a knee brace as recited in claim 1 wherein at least one of said first and said second gear supports includes a stop structure, and wherein said cover and support plate contains at least one stop aperture for insertion of a structure to limit the pivoting angular displacement of said at least one of said first and said second gear supports to thereby limit the angular displacement of said first gear support with respect to said second gear support.

9. The hinge for a knee brace as recited in claim 1 wherein said attachment structure of said first end of said first gear support and said second end of said second gear support are rivet apertures.

10. A knee brace hinge comprising:

a first gear having a first pivot point and a first set of gear teeth having a radial procession with respect to said first pivot point;

a second gear having a second pivot point and a second set of gear teeth having a radial procession with respect to said second pivot point and intermeshing with said first set of gear teeth throughout an intermeshing pivot range, said first and second gears including structure for attachment to an upper and a lower brace support, respectively said first and second gears having a fixed distance from each other; and a cover and support plate for providing adjacent support to said first and said second gears at their first and second pivot points, respectively, and including pivot support structures supported by at least one of said cover and support plate, said first gear and said second gear for pivotally supporting said first gear and said second gear with respect to said cover and support plate said first set of gear teeth radially increasing with respect to said first pivot point and said second set of gear teeth radially decreasing with respect to said second pivot point such that said first set of gear teeth radially increase while said second set of gear teeth radially decrease upon flexing of said first and second gears relative to each other.

11. The hinge for a knee brace as recited in claim 10 wherein said first gear lies adjacent a first smooth section of said first gear and where said second gear lies adjacent a second smooth section of said second gear which interfere with said first smooth section to limit pivoting of said first gear with respect to said second gear.

12. The hinge for a knee brace as recited in claim 10 wherein at least one of said first and said second gear includes a stop structure, and wherein said cover and support plate contains at least one stop aperture for accommodating a structure to limit the pivoting angular displacement of said at least one of said first and said second gear to thereby limit the angular displacement of said first gear with respect to said second gear.

13. The hinge for a knee brace as recited in claim 10 wherein said structure for attachment to an upper and a lower brace support of said first and said second gear supports are rivet apertures.

14. The hinge for a knee brace as recited in claim 10 and further comprising:

a second hinge having first and second gear teeth;

an upper brace support having a first side connected to said first gear of said first hinge and a second side connected to said first gear of said second hinge; and an lower brace support having a first side connected to said second gear of said first hinge and a second side connected to said second gear of said second hinge, said upper and lower braces with said first and second hinges forming a leg brace.

* * * * *